United States Patent [19]

Saito et al.

[11] Patent Number: 4,755,471
[45] Date of Patent: Jul. 5, 1988

[54] TRITIUM RADIOACTIVITY MEASURING SYSTEM

[75] Inventors: Tomo Saito; Kazuo Watanabe; Yumiko Nishiyama, all of Kanagawa; Naotake Morikawa, Tokyo, all of Japan

[73] Assignee: Sagami Chemical Research Center, Tokyo, Japan

[21] Appl. No.: 884,155

[22] Filed: Sep. 5, 1986

Related U.S. Application Data

[62] Division of Ser. No. 454,530, Dec. 30, 1982.

[30] Foreign Application Priority Data

Apr. 30, 1981 [JP] Japan .................. 56-64195

[51] Int. Cl.$^4$ .............................. G01T 1/16
[52] U.S. Cl. .................................... 436/57
[58] Field of Search ............ 436/57, 59, 174, 178

[56] References Cited

U.S. PATENT DOCUMENTS 3,506,402  4/1970  Simon .................. 436/59
3,623,840  11/1971  Benson ................. 436/57
3,945,797  3/1976  Mlinko et al. ........... 436/57

OTHER PUBLICATIONS

Gacs et al.; Automatic Isotope Gas Analysis of Tritium Labelled Organic Materials; J. of Radioanalytical Chem. 45, 1978, pp. 435-444.

Radioassay by Gas Chromatography of Tritium and Carbon-14, Labeled Compounds, Wolfgang et al., Analytical Chemistry, vol. 30, pp. 903-906, 1958.

Low Level Measurement of Tritium by Hydrogenation of Propadiene and Gas Counting of Propane, Wolf et al., Intl. J. Appl. Radiation and Isot., vol. 32, pp. 919-928, 1981.

Chemical Abstract 89:170696m, 1978, Gacs et al.
Chemical Abstract 74:133817w, 1971, Povinec et al.

Primary Examiner—Barry S. Richman
Assistant Examiner—Michael S. Gzybowski
Attorney, Agent, or Firm—Sughrue, Mion, Zinn, Macpeak & Seas

[57] ABSTRACT

A continuous tritium radioactivity measuring system is disclosed, in which a sample gas containing tritium is mixed with hydrogen gas, water vapor and lower hydrocarbon gases with the assistance of a catalyst for causing an isotope exchange reaction between the tritium contained in the sample gas and hydrogen. The resultant tritium gas and lower hydrocarbons containing tritium are removed from the remaining hydrogen water, and radioactivity detection is performed thereon.

10 Claims, 5 Drawing Sheets

TRITIUM RADIOACTIVITY MEASURING SYSTEM

This is a division of application Ser No. 454,530, filed Dec. 30, 1982.

BACKGROUND OF THE INVENTION

The present invention relates to a system for measuring tritium radioactivity.

Tritium radiates soft $\beta$ rays having an average energy of 5.7 KeV. The radioactivity of tritium is generally measured by a batch system using a detector which is filled with a gaseous tritium sample or a liquid scintillator dissolving the sample gas.

The detector used with the batch system for the gaseous tritium sample is a Geiger Muller tube, a proportional counter or an ionization chamber, and the detector for the liquid sample is a liquid scintillation counter.

Although the counting efficiency of the liquid scintillation counter is generally low, it has been widely used because the chemical form of the sample can be relatively freely selected. However, in addition to the low counting efficiency thereof, the liquid scintillation counter is generally very expensive. Furthermore, in the measurement of tritium, there are problems in precise correction for the quenching effect, and with the inflammable radioactive organic liquid left after the measurement. Therefore, it is economically difficult to continuously measure a number of samples by the liquid scintillation counting method and, even if this difficulty is overcome, there are problems of radioactive contamination and safety.

Compared with the liquid scintillation counting method, the measuring method using the ionization chamber, which is theoretically simple in construction and inexpensive in manufacture, is inherently safe. However, it is known that the sensitivity of the ionization chamber is low, and the constituents of the sample whose radioactivity is to be measured are limited.

The method using the proportional counter exhibits considerably higher sensitivity and lower background noise than those of the other systems including the ionization chamber system, and there is no problem in safety management. However, the chemical form of the measurable sample is limited compared with that which can be measured by the ionization chamber system. Therefore, if the limitations in the chemical form of the sample were removed, it would be possible to use the proportional counter system very effectively.

The chemical form of the sample to be measured by the proportional counter system is hydrogen gas or gaseous lower hydrocarbons such as acetylene, ethane, methane or propane, etc., and depends upon the counting characteristics of the counter. These forms are generally provided by using decomposition reactions such as oxidation or reduction, etc., or organic synthesizing reactions together with a decomposition reaction, which requires a troublesome operation under very severe conditions making it practically disadvantageous. Further, it is difficult to prepare these chemical forms continuously through these operations, causing the application thereof to the continuous measuring system to be limited.

SUMMARY OF THE INVENTION

An object of the present invention is to provide a continuous measuring system for tritium radioactivity. The system includes a gaseous sample preparation stage which is inherently safe and simple in operation without producing a considerable amount of radioactive water material.

Another object of the present invention is to provide a continuous measuring system for tritium radioactivity having high sensitivity.

The present system is characterized by contacting a sample gas containing tritium with hydrogen gas, water vapor and gaseous lower hydrocarbons with the assistance of a catalyst maintained at a suitable temperature, to perform an isotope exchange reaction between the tritium in the sample gas and the hydrogen gas and lower hydrocarbon gases, removing the sample gas whose tritium has been exhanged by hydrogen using a suitable separation means such as cooling and/or adsorption, etc., and guiding tritium gas and the lower hydrocarbon gases containing the tritium to a flow type radioactivity detector to measure the radioactivity thereof.

DETAILED DESCRIPTION OF THE PREFERRED EMBODIMENTS

Figure 1:
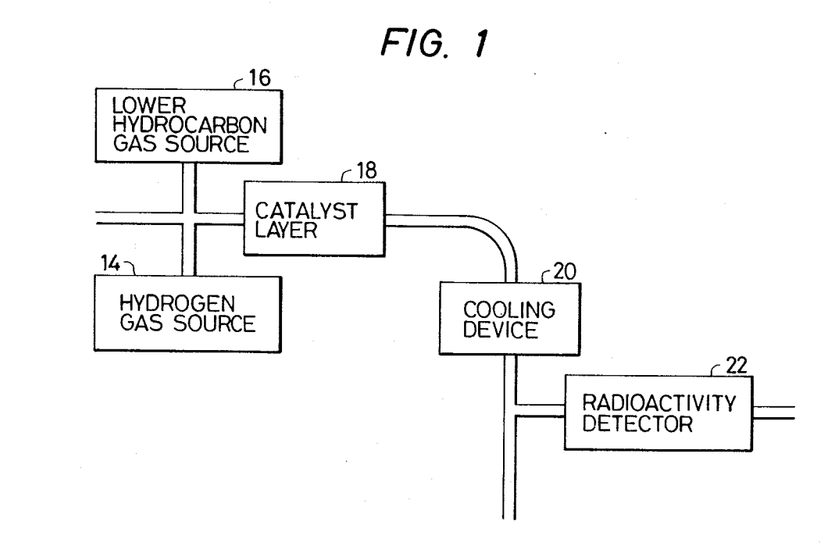
FIG. 1 is a block diagram of an embodiment of the present system.

In FIG. 1, which shows the basic construction of the present invention, hydrogen gas and gaseous lower hydrocarbons such as propane from a hydrogen gas source 14 and a lower hydrocarbon gas source 16, respectively, are added to a gaseous sample containing tritium water ($^3H_2O$) and/or tritium labelled compounds. A mixture of hydrogen gas, lower hydrocarbon gas and the sample gas is introduced into a catalyst layer 18. The catalyst layer 18 is formed of a material such as Pt-$Al_2O_3$ and is maintained at a temperature suitable to cause an isotope exchange reaction. By passing the mixture through the catalyst layer 18, an isotope exchange reaction occurs in the mixture and the tritium contained in the sample gas is replaced by the hydrogen of the hydrogen gas and the lower hydrocarbon gas.

The mixture gas taken out from the catalyst layer 18 is introduced into a cooling device 20 to separate the water content of the sample gas in the mixture gas from the hydrogen and lower hydrocarbon gas and the separated water content is suitably discharged. The remaining tritium gas and lower hydrocarbon gas containing tritium are introduced into the radioactivity detector, i.e., proportional counter 22 and the radioactivity thereof is measured thereby.

According to the present invention, gaseous hydrogen, water and lower hydrocarbons are mixed with the sample gas. The reasons for the addition of such substances to the sample gas and effects thereof will be described with reference to various experiments performed using the system shown in FIG. 1.

EXPERIMENT 1

$C_3H_8$ was used as the lower hydrocarbon and 0.5% $Pt-Al_2O_3$ was used as the catalyst, which was maintained at 220° C. As the sample, liquid phase $^3H_2O$ having a radioactivity of $3.8 \times 10^4$ dpm/μl was injected into an evaporator 10 by a micro syringe to convert it into the gaseous phase, and a radioactivity measurement was performed. The result is shown in Table 1. The radioactivity counted was calculated assuming the counting efficiency of a proportional counter 22 of the long passage type (refer to "Radioiosotopes", Vol 28, 603, 1972) of 93%, from a ratio of the total hydrogen weight of the hydrogen gas and the propane gas to the total hydrogen weight of the mixture gas introduced to the catalyst layer 18.

TABLE 1

| Test No. | $H_2$ (ml/min) | $C_3H_8$ (ml/min) | $^3H_2O$ (mg/min) | Radio-activity ($\times 10^4$ dpm) | Calculated Value ($\times 10^4$ cpm) | Measured Value ($\times 10^4$ cpm) | Efficiency (%) |
|---|---|---|---|---|---|---|---|
| 1 | 16 | 30 | 50 | 9.1 | 5.49 | 4.4 | 80 |
| 2 | 0 | 48 | 50 | 9.1 | 6.74 | 2.9 | 43 |
| 3 | 0 | 48 | 50 | 9.1 | 6.74 | 1.9 | 28 |
| 4 | 0 | 48 | 50 | 9.1 | 6.74 | 1.2 | 18 |
| 5 | 16 | 30 | 50 | 9.1 | 5.49 | 4.4 | 80 |

As will be clear from the above table, in Test No. 1 in which hydrogen gas was added, the counting efficiency was 80%. However, in Test No. 2 performed 30 minutes after the hydrogen gas supply was stopped, the efficiency was reduced to 43% and in the Test No. 3 performed 30 minutes after the Test No. 2 it became 28%. In Test No. 4, which was performed after 30 minutes from the Test No. 3, the efficiency dropped to 18%. Then, 1 hour after Test No. 4, the hydrogen gas supply was started again and the counting efficiency was increased to 80%. Thus, the effect of the hydrogen is remarkable. That is, it may be that the added hydrogen gas acts as not only the exchange gas for tritium but also as a catalyst assistant.

EXPERIMENT 2

In order to clarify the effect of the addition of water, $^3H$-toluene was used as a sample, and hydrogen gas and water were added with the amount of water being variable. The width and half-width of the output of the radioactivity detector were measured. The catalyst and the temperature thereof were the same as those in Experiment 1 and helium was used as the carrier gas. The result of the measurement is shown in Table 2.

TABLE 2

| No. | $H_2O$ (μl/min) | $H_2$ (ml/min) | $C_3H_8$ (ml/min) | He (ml/min) | Width (mm) | Half-Width (mm) |
|---|---|---|---|---|---|---|
| 1 | 0 | 24 | 63 | 18 | 35 | 14 |
| 2 | 0 | 8 | 33 | 18 | 50 | 13 |
| 3 | 40 | 16 | 61 | 0 | 14 | 5 |

From Table 2, it is clear that when water is added, both the width and half-width of the counter output are remarkably reduced, showing the smoothening of the movement of the tritium along the catalyst. That is, it is known that catalysts which are effective for the exchange reaction usually contain a large amount of hydrogen, which makes smooth movements difficult. By continuously adding water, the movements may become smoothened and, thus, the present system is able to respond with high sensitivity to a variation of sample concentration.

EXPERIMENT 3

On the basis of Experiments 1 and 2, the radioactivity measurement was performed for tritium gas and a tritium labelled lower hydrocarbon produced by a hydrogen isotope exchange reaction on the catalyst between a gaseous tritium labelled compound and a gaseous mixture of hydrogen, a lower hydrocarbon and water. The result is shown in Table 3.

In this experiment, methane, propane, isobutane and n-butane were used as lower hydrocarbons, respectively, and 1% $Pt-Al_2O_3$ (13 ml) and 10% $Ni-Al_2O_3$ (13 ml) were used as the catalyst, respectively. A catalyst tube having a diameter of 4 mm and a length of 10 cm was filled with either catalyst and maintained at 200° to 250° C. Tritium labelled compound was injected thereto using a micro syringe and the counting efficiency was calculated as in Experiment 1.

TABLE 3

| $H_2O$ (ml/min) | $H_2$ (ml/min) | Lower Hydrocarbon (ml/min) | Catalyst | Temperature (°C.) | Sample | Radio-activity $\times$ 10 (dpm) | Calculated Value $\times$ 10 (cpm) | Measured Value $\times$ 10 (cpm) | Efficiency |
|---|---|---|---|---|---|---|---|---|---|
| 17 | 15 | $C_3H_8$ 66 | 1% Pt—$Al_2O_3$ | 250 | $^3H_2O$ | 8.92 | 7.63 | 7.36 | 0.96 |
| 17 | 15 | $C_3H_8$ 66 | 1% Pt—$Al_2O_3$ | 250 | $^3H$—toluene | 4.87 | 4.17 | 4.19 | 1.00 |
| 17 | 14 | $C_3H_8$ 69 | 1% Pt—$Al_2O_3$ | 250 | $^3H$—toluene | 2.90 | 2.51 | 2.25 | 0.90 |
| 17 | 14 | $C_3H_8$ 69 | 1% Pt—$Al_2O_3$ | 250 | $^3H$—methanol | 7.72 | 6.68 | 2.07 | 0.31 |
| 17 | 14 | $C_3H_8$ 69 | 1% Pt—$Al_2O_3$ | 250 | $^3H$—n-hexadecane | 2.08 | 1.79 | 2.70 | 0.15 |
| 17 | 14 | $CH_4$ 64 | 1% Pt—$Al_2O_3$ | 250 | $^3H_2O$ | 8.73 | 6.98 | 2.33 | 0.33 |
| 17 | 14 | $CH_4$ 64 | 1% Pt—$Al_2O_3$ | 250 | $^3H$—toluene | 8.90 | 7.11 | 1.88 | 0.26 |
| 17 | 14 | $CH_4$ 64 | 1% Pt—$Al_2O_3$ | 250 | $^3H$—methanol | 11.35 | 9.08 | 3.49 | 0.38 |
| 17 | 14 | $CH_4$ 64 | 1% Pt—$Al_2O_3$ | 250 | $^3H$—methanol | 7.26 | 5.81 | 1.52 | 0.26 |
| 17 | 14 | $CH_4$ 64 | 1% Pt—$Al_2O_3$ | 250 | $^3H$—n-hexadecane | 2.08 | 1.66 | 2.10 | 0.13 |
| 17 | 14 | n-$C_4H_{10}$ 68 | 1% Pt—$Al_2O_3$ | 250 | $^3H_2O$ | 5.50 | 4.81 | 4.63 | 0.96 |
| 50 | 14 | n-$C_4H_{10}$ 68 | 1% Pt—$Al_2O_3$ | 250 | $^3H_2O$ | 4.56 | 3.56 | 3.77 | 1.06 |
| 50 | 14 | n-$C_4H_{10}$ 68 | 1% Pt—$Al_2O_3$ | 250 | $^3H$—methanol | 7.72 | 6.03 | 1.02 | 0.17 |
| 50 | 14 | iso-$C_4H_{10}$ 66 | 1% Pt—$Al_2O_3$ | 250 | $^3H_2O$ | 5.31 | 4.14 | 3.81 | 0.93 |
| 50 | 14 | iso-$C_4H_{10}$ 66 | 1% Pt—$Al_2O_3$ | 250 | $^3H$—methanol | 7.75 | 6.19 | 0.97 | 0.16 |
| 50 | 14 | iso-$C_4H_{10}$ 66 | 1% Pt—$Al_2O_3$ | 250 | $^3H$—toluene | 3.00 | 2.34 | 1.07 | 0.46 |

TABLE 3-continued

| H$_2$O (ml/min) | H$_2$ (ml/min) | Lower Hydrocarbon (ml/min) | Catalyst | Temperature (°C.) | Sample | Radioactivity × 10 (dpm) | Calculated Value × 10 (cpm) | Measured Value × 10 (cpm) | Efficiency |
| --- | --- | --- | --- | --- | --- | --- | --- | --- | --- |
| 17 | 13 | C$_3$H$_8$68 | 10% Ni—Al$_2$O$_3$ | 250 | $^3$H$_2$O | 5.31 | 4.59 | 3.24 | 0.70 |
| 17 | 13 | C$_3$H$_8$68 | 10% Ni—Al$_2$O$_3$ | 250 | $^3$H—toluene | 4.97 | 4.30 | 1.75 | 0.41 |

Although there are differences in the counting efficiency among tritium labelled compounds, it will be clearly understood that the radioactivity of tritium labelled compounds other than tritium water can also be continuously measured using the isotope exchange reaction on the catalyst with hydrogen gas and lower hydrocarbons.

Figure 2:
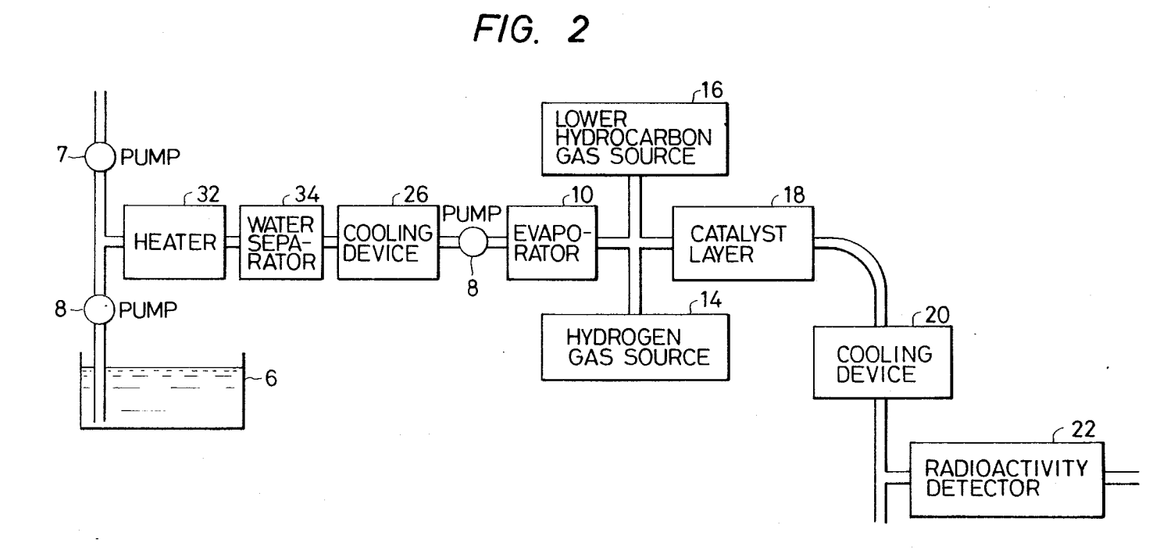
FIG. 2 is a block diagram of a second embodiment of the present system.

FIG. 2 shows another embodiment of the present invention. This embodiment is very effective in measuring the radioactivity of tritium water using water which contains tritium water as a sample in a container 6. The water containing the tritium water may be waste water containing non-volatile substances.

In the embodiment of FIG. 2, the sample water supplied through a pump 8 is mixed with air supplied through a pump 7 and then the air-sample mixture is fed to a heater 32. The mixture from the heater 32 which contains heated air and vaporized sample water is fed to a water separator 34 in which any excess amount of sample water is separated and drained. Air containing a predetermined amount of sample water is guided to a cooling device 26. The vapor component is cooled and condensed to separate it from the air which is exhausted. The condensed water is fed to an evaporator 10 by the pump 8. The radioactivity of the water vapor from the evaporator 10 is measured through the system mentioned with reference to FIG. 1.

Figure 3:
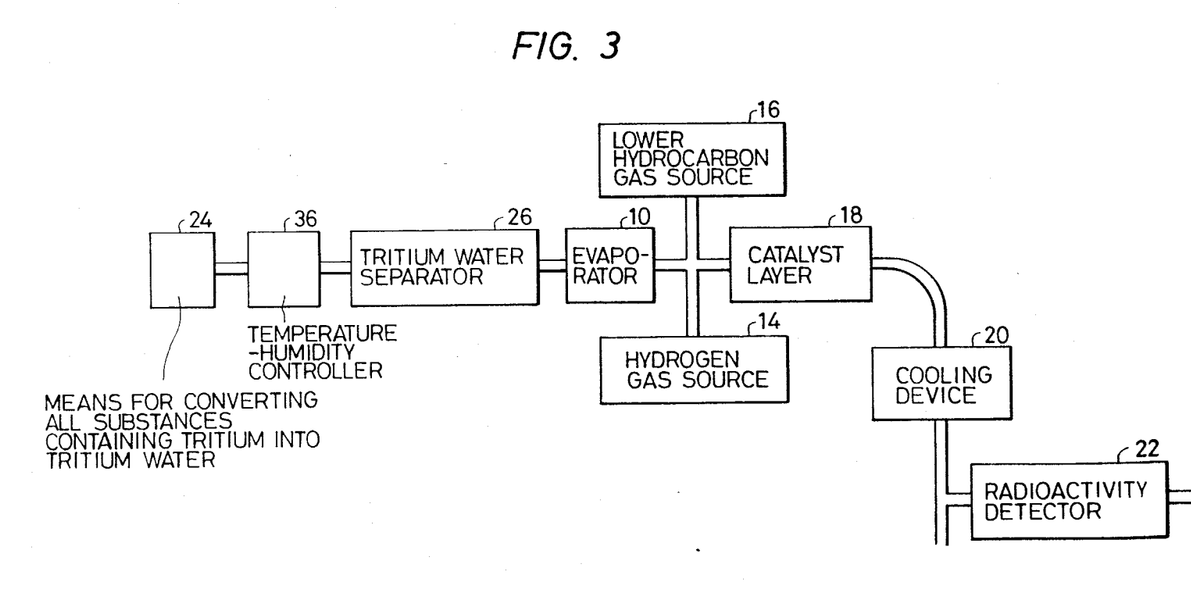
FIG. 3 is a block diagram of a third embodiment of the present system.

FIG. 3 shows another embodiment of the present invention, which is effective in continuously monitoring tritium in air. Tritium contained in air usually takes the forms of tritium gas and/or tritium water. In the embodiment shown in FIG. 3, means 24 for converting all substances containing tritium into tritium water is provided, to which air is supplied. As the means 24, a means for oxidizing the decomposing substances contained in air or a means for assisting isotope exchange reactions between hydrogen and tritium may be used. Air containing tritium water from the means 24, the temperature and humidity of which is regulated by a temperature-humidity controller 36 to predetermined values, is guided to a tritium water separator 26 to separate the latter from the air. Tritium water from the separator 26 is fed to the evaporator 10 and the radioactivity thereof is measured continuously as in the embodiment in FIG. 2.

Figure 4:
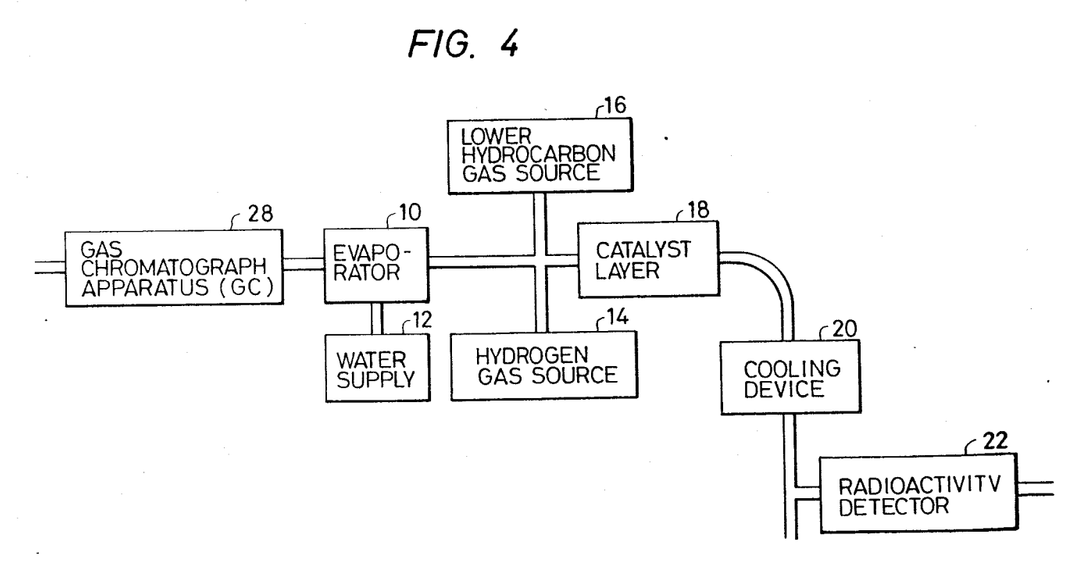
FIG. 4 is a block diagram of a fourth embodiment of the present system.

FIG. 4 shows another embodiment of the present invention, in which the radioactivity of tritium contained in components successively flowing from a gas chromatograph apparatus (GC) 28 is continuously measured. The components, each containing labelled compounds from the GC 28, are supplied to the evaporator 10 and the radioactivity thereof is measured as in the embodiment of FIG. 1. Although, in this embodiment, the components from the GC 28 are directly introduced into the counter 22, these components may be converted into tritium water by passing them through an oxidation furnace (CuO) and the oxidized components may be introduced into the counter.

Figure 5:
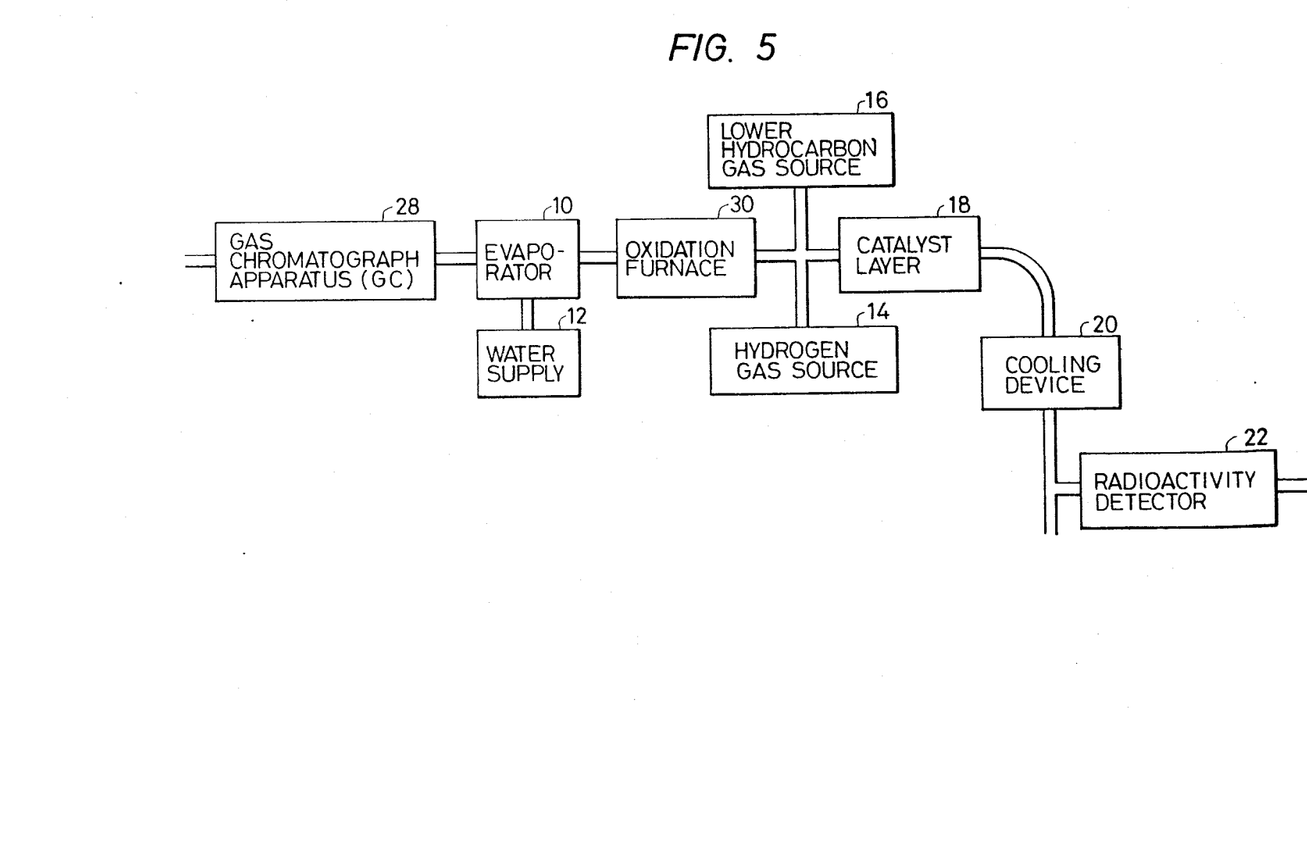
FIG. 5 is a block diagram of a fifth embodiment of the present system.

FIG. 5 shows another embodiment similar to that of FIG. 4.

When the present invention using the isotope exchange reaction is applied to the gas chromatograph shown in FIG. 4 or 5, the conditions necessary to introduce reactions are not as severe as are required in the conventional system in which the reduction of tritium water by means of iron or carbon, or the hydrodecomposition of organic substances in hydrogen gas flow, etc., is used. Therefore, the present system can work stably, and the energy consumption thereof is relatively small.

Further, when the system is such that the amount of hydrogen continuously supplied for exchange with the tritium is considerably larger than the amount of the sample from the GC, the stoichiometric amount of tritium labelled substances flowing from the GC becomes negligible, and therefore the tritium may be isotope-exchanged and measured substantially according to the hydrogen partition law between water and a combination of hydrogen and propane.

As mentioned, the present invention is characterized by the radioactivity measurement of tritium in which the isotope exchange reaction is carried out by mixing the sample gas containing tritium with hydrogen gas, water and lower hydrocarbons under the assistance of a suitable catalyst. The sample gas after the isotope exchange reaction is properly removed, and the remaining hydrogen gas and lower hydrocarbon gases which contain tritium are conducted into the radioactivity detector.

Since the larger the carbon content of the lower hydrocarbons, which act, together with the hydrogen gas, as the counting gas, the greater the effect of the partition law according to which the tritium is moved to the lower hydrocarbons (and hydrogen), the radioactivity per unit volume of hydrocarbon gas (and hydrogen gas), and hence the detection sensitivity becomes higher. Therefore, the number of carbon atoms of the lower hydrocarbons should be as large as possible. However, the vapor pressure thereof may be lowered when the number of carbon atoms is too large. Therefore, this value should be suitably selected to satisfy these contradictory requirements. It has been found that hydrocarbons having carbon atoms in a number of 5 or less may be suitable.

As to the catalyst, Pt-Al$_2$O$_3$ and Ni-Al$_2$O$_3$ have been described as examples. However, it has been found that other catalysts such as Co-SiO$_2$ can be used with similar effects.

It is clear that higher catalyst temperatures provide a better effect, but the temperature should be kept low enough to facilitate temperature control. It has been found that the catalyst temperature may be as low as 200° C. to 300° C. with satisfactory results.

Further, it has been found that the present system measures radioactivity with an accuracy of more than two digits better than the conventional measuring system using the ionization chamber.

EXPERIMENT 4

Tritium water of low concentration ($4.5 \times 10^{-5}$ μCi/ml) was conducted to the system shown in FIG. 1 at a rate of 200 to 800 μl/min. Isotope exchange of tritium with the hydrogen of hydrogen gas (flow rate: 11 ml/min) and propane gas: (flow rate 70 ml/min) was performed at 250° C. through a catalyst tube having a diameter of 8 mm and a length of 50 cm and filled with Pt-Al$_2$O$_3$, and the radioactivity measurement was conducted using the counting tube as in Experiment 1. The results are shown in Table 4.

TABLE 4

| H$_2$O (mg/min) | H$_2$ (ml/min) | C$_3$H$_8$ (ml/min) | Specific Radio-activity of $^3$H$_2$O × $10^{-5}$ (μCi/ml) | Measured Value (cpm) |
|---|---|---|---|---|
| 200 | 11 | 70 | 4.5 | 95 |
| 350 | 11 | 70 | 4.5 | 126 |
| 800 | 11 | 70 | 4.5 | 123 |

Although the radioactivity detected was only around 100 cpm, it was clearly quantitatively measured. Since the detection limit of tritium in continuous waste water monitoring using the conventional plastic scintillator is $2.2 \times 10^{-3}$ μCi/ml, the present system makes the continuous detection of tritium water possible with a sensitivity of about 50 times that of the conventional system.

Further, when a radioactivity measurement for tritium water of low concentration separated from air maintained at 40° C. and having a relative humidity of 90% is performed using the embodiment shown in FIG. 3, the radioactivity of the tritium water as converted into the tritium density in air becomes $2.3 \times 10^{-9}$ μCi/cm$^3$. Therefore, the tritium measurement sensitivity of the present invention is about 200 times the detection limit ($5 \times 10^{-7}$ μCi/cm$^3$), of the continuous air monitor using the conventional ionization chamber.

EXPERIMENT 5

A mixture of water, hydrogen gas and propane gas is passed along a catalyst tube having a diameter of 14 mm and a length of about 20 cm. The catalyst tube is filled with 14.2 grams of 0.5% Pt-carbon maintained at 250° C. or the same amount of 0.5% Pd-carbon maintained at 250° C. Tritium water was added to the mixture by a micro syringe and the radioactivity of the tritium in the tritium labelled propane gas and the tritium gas produced by the hydrogen isotope exchange reaction was measured. The results are shown in Table 5.

TABLE 5

| H$_2$ (ml/min) | C$_3$H$_8$ (ml/min) | H$_2$O (g/min) | Catalyst | Radio-activity (dpm × $10^{-3}$) | Measured Value (cpm × $10^{-3}$) | Efficiency |
|---|---|---|---|---|---|---|
| 27 | 73 | 0.52 | 0.5% Pt-carbon | 1.01 | 0.73 | 0.72 |
| 27 | 73 | 0.54 | 0.5% Pt-carbon | 0.98 | 0.70 | 0.71 |
| 10 | 77 | 0.54 | 0.5% Pt-carbon | 1.80 | 1.42 | 0.79 |
| 10 | 76 | 0.54 | 0.5% Pt-carbon | 1.75 | 1.42 | 0.81 |
| 10 | 76 | 0.55 | 0.5% Pd-carbon | 1.74 | 0.76 | 0.44 |
| 10 | 77 | 0.55 | 0.5% Pd-carbon | 1.74 | 0.70 | 0.40 |

What is claimed is:

1. A method of quantitatively measuring the radioactivity of a tritium-containing sample, comprising; mixing a gaseous tritium-containing sample together with a gaseous combination comprising hydrogen, water and at least one lower hydrocarbon gas; forwarding said mixture into a catalyst chamber where said mixture is contacted with an isotope exchange reaction promoting catalyst; causing, by means of said catalyst, an isotope exchange reaction between the tritium of said sample and hydrogen atoms contained in said gaseous combination; separating tritium gas and tritium-containing lower hydrocarbon gas formed as a result of isotope exchange, from water formed during or remaining after said isotope exchange; and measuring the radioactivity of said tritium gas and tritium-containing lower hydrocarbon gas by means of a proportional counter.

2. A process as claimed in claim 1, further comprising the preliminary step of converting a tritium-containing liquid sample into said gaseous tritium-containing sample by means of an evaporator.

3. A method as claimed in claim 1, wherein said catalyst is selected from the group consisting of a platinum containing catalyst and a nickel containing catalyst, and wherein said catalyst is maintained at a temperature between 200° and 250° C. during said isotope exchange.

4. A method as claimed in claim 1, further comprising the preliminary step of receiving a tritium-containing sample in liquid form, mixing said sample with air, heating said air-sample mixture, cooling and condensing said mixture to separate said air, and evaporating said condensate to form said gaseous tritium-containing sample.

5. A method as claimed in claim 1, further comprising the preliminary step of receiving a tritium-containing sample in the form of tritium gas or a combination of tritium gas and tritium water, converting the tritium-containing substances of said sample into tritium water, and evaporating said tritium water to form said gaseous tritium-containing sample.

6. A method as claimed in claim 5, wherein the step of converting said tritium-containing substances into tritium water comprises promoting an isotope exchange reaction between the tritium of said tritium-containing substances and hydrogen.

7. A method as claimed in claim 5, wherein said step of converting said tritium-containing substances into tritium water comprises oxidizing said tritium-containing substances.

8. A method as claimed in claim 1, further comprising the preliminary steps of receiving tritium-containing samples from a gas chromatograph apparatus, forwarding said samples, along with a supply of water, to an evaporator, and, in said evaporator, converting said samples into said gaseous tritium-containing samples.

9. A method as claimed in claim 8 further comprising the step of passing said samples from said gas chromatograph apparatus through an oxidation furnace to convert said tritium-containing samples into tritium water.

10. A method as claimed in claim 9 wherein said oxidation furnace is disposed at the output of said evaporator.

* * * * *